United States Patent
Wulfman et al.

(10) Patent No.: US 9,345,873 B2
(45) Date of Patent: May 24, 2016

(54) LEAD WITH TEXTURED INSULATIVE LAYER

(71) Applicant: Cardiac Pacemakers, Inc., St. Paul, MN (US)

(72) Inventors: David R. Wulfman, Minneapolis, MN (US); Rahul K. Rajgarhia, Forest Lake, MN (US); David J. Smith, Shoreview, MN (US); Tolga Tas, Shoreview, MN (US); Daniel J. Cooke, Roseville, MN (US); Christopher R. Perrey, Victoria, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/957,970

(22) Filed: Aug. 2, 2013

(65) Prior Publication Data
US 2014/0052226 A1  Feb. 20, 2014

Related U.S. Application Data

(60) Provisional application No. 61/683,109, filed on Aug. 14, 2012.

(51) Int. Cl.
*A61N 1/05* (2006.01)
*H01R 43/16* (2006.01)

(52) U.S. Cl.
CPC *A61N 1/05* (2013.01); *H01R 43/16* (2013.01); *Y10T 29/49174* (2015.01)

(58) Field of Classification Search
CPC ...................................................... A61N 1/05
USPC ............................................ 607/116, 122, 127
See application file for complete search history.

(56) References Cited

U.S. PATENT DOCUMENTS

| 5,244,619 A | 9/1993 | Burnham |
| 5,762,631 A | 6/1998 | Klein |
| 5,968,087 A * | 10/1999 | Hess et al. .................... 607/127 |
| 6,249,708 B1 * | 6/2001 | Nelson et al. ................ 607/122 |

(Continued)

FOREIGN PATENT DOCUMENTS

| CN | 101594907 A | 12/2009 |
| JP | H10118188 A | 5/1998 |

(Continued)

OTHER PUBLICATIONS

International Search Report and Written Opinion issued in PCT/US2013/053472, mailed Jun. 11, 2013, 13 pages.

(Continued)

*Primary Examiner* — Theodore Stigell
*Assistant Examiner* — Nadia A Mahmood
(74) *Attorney, Agent, or Firm* — Faegre Baker Daniels LLP (57) ABSTRACT

Described is a medical device lead including a lead body having a conductor lumen including an inner surface. The lead also includes a conductor assembly extending through the conductor lumen; the conductor assembly comprising a conductor member and an outer insulative layer; and an electrode coupled to the conductor cable. The outer insulative layer includes a textured external surface that reduces the coefficient of friction between the outer insulative layer and the inner surface of the conductor lumen through which the conductor assembly extends. Methods of forming the conductor assembly are also described.

19 Claims, 12 Drawing Sheets

(56) References Cited

U.S. PATENT DOCUMENTS

| | | |
|---|---|---|
| 6,925,334 B1 | 8/2005 | Salys |
| 7,877,151 B2 | 1/2011 | Wengreen et al. |
| 2002/0058979 A1* | 5/2002 | Sass .............................. 607/116 |
| 2006/0211979 A1 | 9/2006 | Smith et al. |
| 2007/0256696 A1 | 11/2007 | Buchman et al. |
| 2010/0331936 A1 | 12/2010 | Perrey et al. |
| 2014/0052108 A1 | 2/2014 | De Kock et al. |

FOREIGN PATENT DOCUMENTS

| | | |
|---|---|---|
| JP | 2008513180 A | 5/2008 |
| WO | WO2009035708 A1 | 3/2009 |

OTHER PUBLICATIONS

International Preliminary Report on Patentability issued in PCT/US2013/053472, mailed Feb. 17, 2015, 8 pages.

* cited by examiner

LEAD WITH TEXTURED INSULATIVE LAYER

CROSS-REFERENCE TO RELATED APPLICATION

This application claims priority to Provisional Application No. 61/683,109, filed Aug. 14, 2012, which is herein incorporated by reference in its entirety.

TECHNICAL FIELD

The present disclosure relates to medical devices. More particularly, the present disclosure relates to adding surface texture to a component of a medical device in order to improve device longevity and performance.

BACKGROUND

The implantation of medical devices has become a relatively common technique for treating a variety of medical or disease conditions within a patient's body. Depending upon the conditions being treated, today's medical implants can be positioned within specific portions of a patient's body where they can provide beneficial functions for periods of time ranging from days to years. There is a continuing need for improved medical implants and associated delivery instruments.

SUMMARY

Example 1 is an implantable medical lead comprising a lead body, a conductor assembly and an electrode on the lead body coupled to the conductor member. The lead body has a conductor lumen having a substantially smooth inner surface. The conductor assembly extends through the conductor lumen and includes a conductor member and an outer insulative layer disposed about the conductor member. The outer insulative layer includes a textured external surface. In various embodiments, the textured external surface of the outer insulative layer is configured to minimize friction between the textured external surface and the substantially smooth inner surface of the conductor lumen.

In Example 2, the implantable medical lead of Example 1, wherein the textured external surface includes a plurality of raised surface features.

In Example 3, the implantable medical lead of Example 2, wherein the plurality of raised surface features extend longitudinally along the conductor assembly.

In example 4, the implantable medical lead of Examples 2 or 3, wherein the raised surface features extend in a helical pattern longitudinally along the conductor assembly.

In Example 5, the implantable medical lead of any of Examples 1-4, wherein the outer insulative layer comprises a polymeric element extruded about the conductor member.

In Example 6, the implantable medical lead of any of Examples 1-4, wherein the outer insulative layer comprises a polymeric element molded about the conductor member.

In Example 7, the implantable medical lead of any of Examples 1-6, wherein the outer insulative layer has a cross-sectional shape defined by a plurality of generally flat surface segments arranged about a longitudinal axis of the conductor assembly, with a ridge disposed between adjacent generally flat surface segments.

In Example 8, the implantable medical lead of any of Examples 1-7, wherein the conductor member comprises a multi-strand cable or wire coil about which the outer insulative layer is extruded.

In Example 9, the implantable medical lead of any of Examples 1-8, wherein the textured external surface has a surface roughness greater than a surface roughness of the inner surface of the conductor lumen.

Example 10 is a method of forming an implantable medical lead. The method comprises forming a conductor assembly by extruding a tubular polymeric outer insulative layer over a conductor member through an extrusion die configured to form a textured external surface on the outer insulation layer. The method further comprises disposing the conductor assembly within a conductor lumen of an insulative lead body, wherein the conductor lumen has a substantially smooth inner surface, coupling an electrode to the conductor member and the lead body. The textured external surface of the outer insulative layer is configured to minimize frictional forces between the textured external surface and the inner surface of the conductor lumen.

In Example 11, the method of Example 10, wherein forming the conductor assembly includes extruding the tubular polymeric outer insulative layer having a cross-sectional shape defined by a plurality of generally flat surface segments arranged about a longitudinal axis of the conductor assembly, with a ridge disposed between adjacent generally flat surface segments.

In Example 12, the method of Example 10, wherein the textured external surface is characterized in part by a plurality raised surface features that extend longitudinally along the conductor assembly.

In Example 13, the method of any of Examples 10-12, wherein the textured external surface is characterized in part by a plurality of raised surface features that extend in a helical pattern longitudinally along the conductor assembly.

Example 14 is a method of forming an implantable medical lead. The method comprises the steps of disposing a tubular-shaped polymeric outer insulative layer onto a conductor member, and adding a surface texture to at least a portion of an outer surface of the outer insulative layer. The method further comprises disposing the conductor member with the outer insulative layer disposed thereon within a conductor lumen of an insulative lead body, wherein the conductor lumen has a substantially smooth inner surface, coupling an electrode to the conductor member and the lead body, and wherein the surface texture is configured to minimize friction between the outer insulative layer and the inner surface of the conductor lumen.

In Example 15, the method of Example 14, wherein the step of adding the surface texture to the outer surface of the outer insulative layer comprises passing the conductor member and insulative layer together through a die that is configured to add the surface texture to the outer surface of the outer insulative layer.

In Example 16, the method of Example 14-15, wherein the texture includes a plurality of raised surface features.

In Example 17, the method of any of Examples 14-16, wherein adding the surface texture to at least a portion of the outer surface of the outer insulative layer includes forming the outer insulative layer having a cross-sectional shape defined by a plurality of generally flat surface segments arranged about a longitudinal axis of the conductor assembly, with a ridge disposed between adjacent generally flat surface segments.

In Example 18, the method of any of Examples 14-17, wherein the step of disposing the outer insulative layer onto the conductor member includes extruding the outer insulative layer onto the conductor member.

In Example 19, the method of any of Examples 14-17, wherein the step of disposing the outer insulative layer onto the conductor member includes molding the outer insulative layer onto the conductor member.

In Example 20, the method of any of Examples 14-19, wherein the conductor member comprises a multi-strand cable.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The invention, however, is not limited to the particular embodiments described. On the contrary, the invention is intended to cover all modifications, equivalents, and alternatives falling within the scope of the invention as defined by the appended claims.

DETAILED DESCRIPTION

Figure 1:
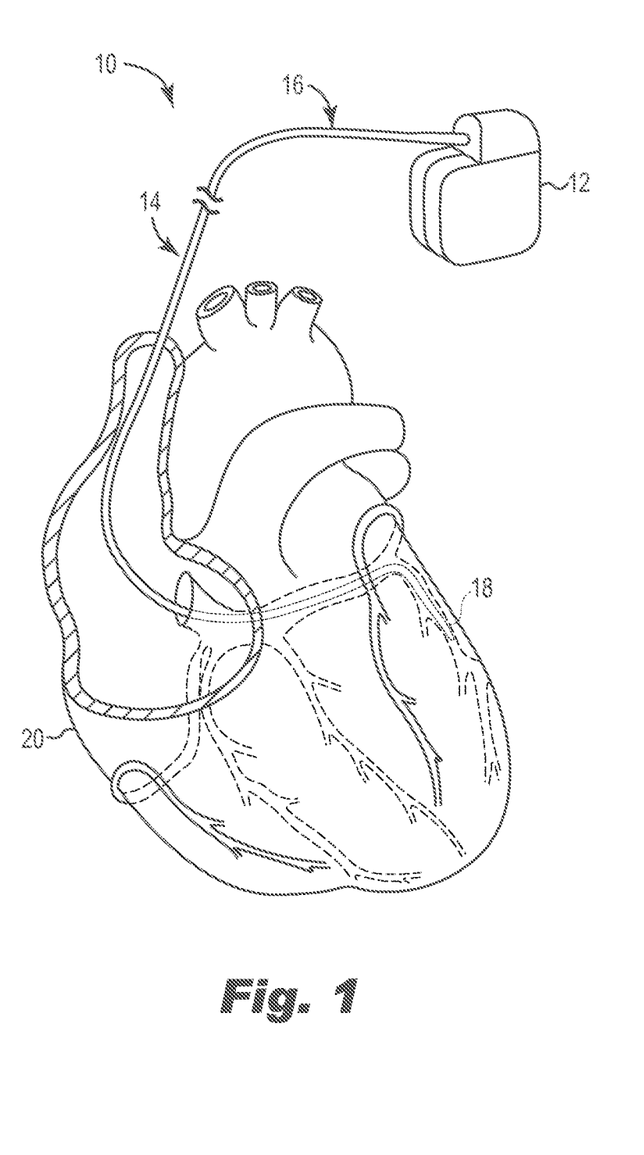
FIG. 1 is a schematic view of heart with a lead system implanted according to one embodiment.

FIG. 1 is a schematic view of a cardiac rhythm management system 10 including an implantable medical device (IMD) 12 and an implantable medical lead 14 in an implanted position with respect to a patient's heart 20 according to one embodiment. As shown, the IMD 12 can include a pulse generator such as a pacemaker, a cardioverter/defibrillator, a cardiac resynchronization therapy (CRT) device, or a CRT device with defibrillation capabilities (a CRT-D device), among other appropriate IMDs 12. In the illustrated embodiment, the IMD 12 can be a CRT or CRT-D device. In various embodiments, the IMD 12 can be implanted subcutaneously within the body, for example, at a location such as in the patient's chest or abdomen, although other implantation locations are possible.

The lead 14 is a flexible, elongate structure and, as shown in FIG. 1, includes a proximal end 16 and a distal end 18. In the illustrated embodiment, the proximal end 16 is coupled to or formed integrally with the IMD 12, and the distal end 18 of the lead 14, in turn, is implanted in a coronary vein adjacent to the left ventricle of the heart 20 so as to facilitate stimulation of the left ventricle. In various embodiments, additional leads (not shown in FIG. 1) can be implanted in or adjacent to other regions of the heart 20, e.g., the right atrium or right ventricle, or on the epicardial surface of the heart 20, based on the particular clinical needs of the patient. While not shown in FIG. 1, as explained in greater detail herein, the lead 14 includes one or more electrodes and one or more conductors coupled to each electrode to electrically couple the electrode with the IMD 12 for sensing intrinsic cardiac activity and providing electrical stimuli to the cardiac tissue.

Figure 2:
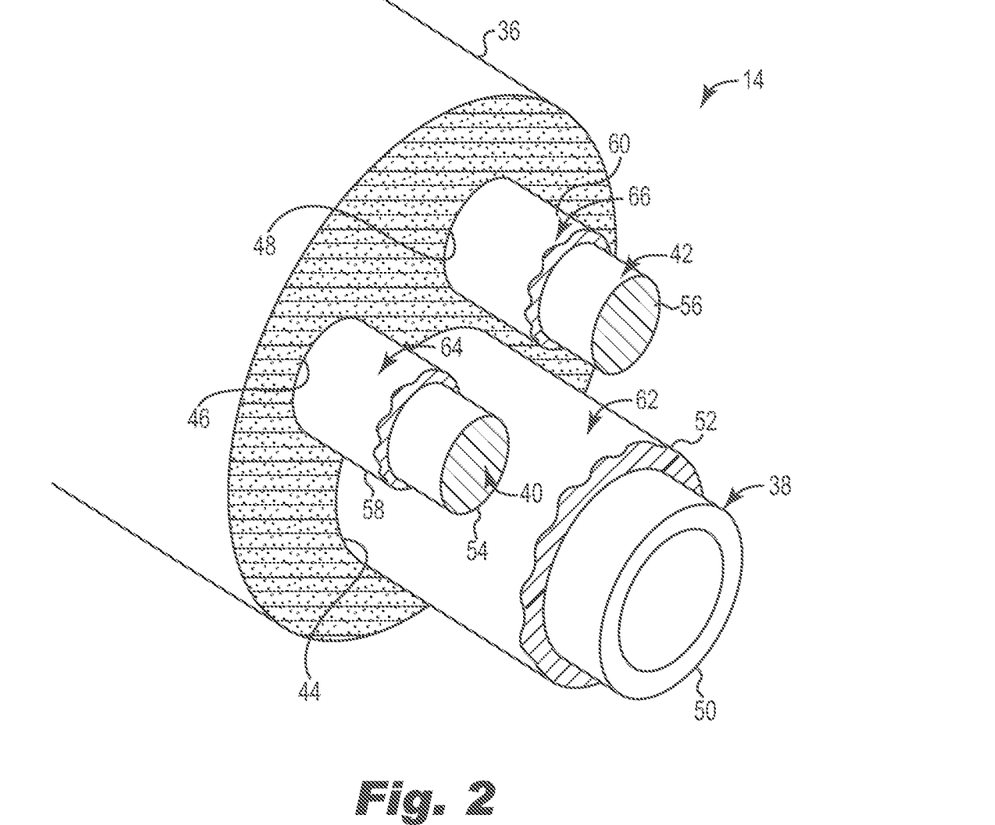
FIG. 2 is a perspective view of a lead of the lead system of FIG. 1 according to one embodiment.
Figure 3:
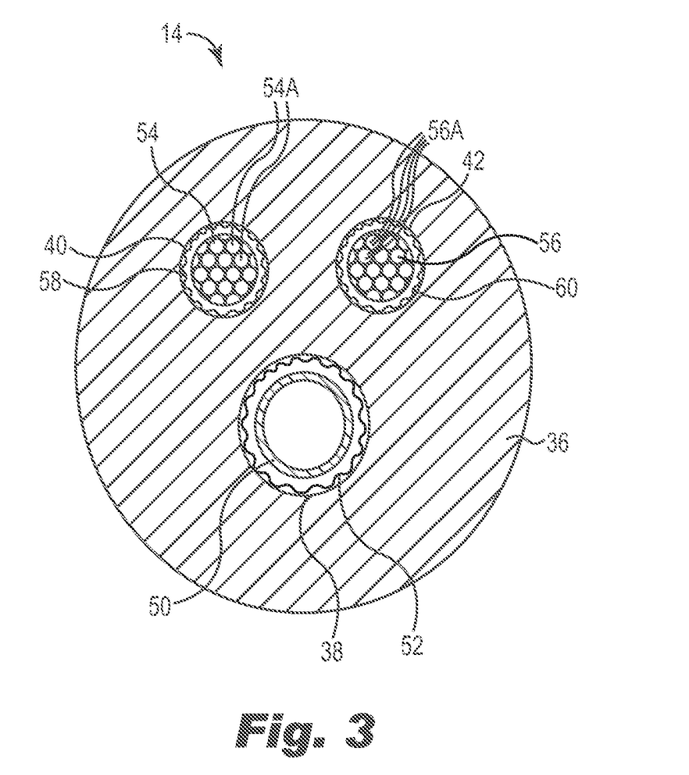
FIG. 3 is a cross-sectional view of the lead of FIG. 2.

FIGS. 2 and 3 are perspective and cross-sectional views, respectively, of a portion of the lead 14. As shown, the lead 14 includes a lead body 36 and an exemplary arrangement of first, second and third conductor assemblies 38, 40, 42 extending there through. In various embodiments, the lead body 36 is a flexible tubular body that defines a coil conductor lumen 44 and two wire conductor lumens 46, 48 extending between the proximal and distal ends 16, 18 of the lead 14 (see FIG. 1). As further shown, the first, second and third conductors 38, 40, 42 extend, respectively, through the first, second and third lumens, 44, 46, 48. In various embodiments, each of the lumens 44, 46, 48 has, in the various embodiments, an inner surface that is substantially smooth. In various embodiments, the aforementioned substantially smooth inner surfaces each have a roughness average (Ra) of less than 10 microinches.

Additionally, while the particular lead 14 illustrated includes three (3) lumen/conductor assembly combinations, in various other embodiments the lead 14 can include either more or fewer lumens and conductors, depending on the type of the IMD and the clinical needs of the patient.

The lead body 36 can be made from a flexible, biocompatible material suitable for lead construction. In various embodiments, the lead body 36 is made from a flexible, electrically insulative material. In one embodiment, the lead body 36 can be made from silicone rubber. In another embodiment, the lead body 36 can be made from polyurethane. In various embodiments, respective segments of the lead body can be made from different materials, so as to tailor the lead body characteristics to its intended clinical and operating environments.

In the various embodiments, the conductors of the lead 14 can be low voltage or high voltage conductors. As used herein, "low voltage" conductors generally refer to conductors that are configured for low-voltage functions, such as sensing and pacing. "High voltage" conductors refer to conductors that are configured to conduct current at high voltages, as is required during defibrillation therapy, for example. The conductors can be cable conductors or coiled conductors. A coiled conductor is generally helical in configuration and includes one or more conductive wires or filaments. A cable conductor has a substantially linear configuration and can also include a plurality of conductive wires or filaments.

As shown in FIGS. 2 and 3, the conductor assembly 38 includes a conductor member 50 and an outer insulative layer 52 disposed about the conductor member 50. In the illustrated embodiment, the conductor member 50 is a low voltage conductor coil and can be part of a system configured to provide pacing or CRT stimuli and/or to sense intrinsic cardiac electrical activity. Thus, in the various embodiments, the conductor member 50 can be coupled to a low voltage electrode (not shown) for facilitating the aforementioned stimulation and sensing functions.

As further shown, the conductor assemblies 40, 42 include, respectively, conductor members 54, 56, which in turn, respectively, have outer insulative layer 58, 60 disposed thereabout. As shown in the embodiment illustrated in FIG. 2, the conductor members 40, 42 can comprise a single wire. Alternatively, as shown in the embodiment of FIG. 3, the conductor members 54, 56 can be in the form of multi-strand cable conductors including, respectively, a plurality of wires 54A, 56A. The conductor members 54, 56 can, in various embodiments, be configured for high voltage applications such as antitachyarrhythmia therapy or cardioverter/defibrillator therapy systems, in which case they would each be coupled to at least one relatively large defibrillation coil electrode. Alternatively, the conductor members 54, 56 can also be used in low voltage applications similar to those described previously with respect to the conductor member 50. In the various embodiments, the conductor members 50, 54 and/or 56 can be made of a suitable electrically conductive material such as Elgiloy, MP35N, tungsten, tantalum, iridium, platinum, titanium, palladium, stainless steel, as well as alloys of these materials.

In the various embodiments, the outer insulative layers 52, 58, 60 are configured to have, respectively, textured external surfaces 62, 64 and 66. As shown, the textured external surfaces 62, 64 and 66 are disposed opposite the respective conductive member, and can contact the substantially smooth inner surface of the conductor lumen in which the particular conductor assembly is disposed.

FIGS. 2 and 3 illustrate, schematically, an exemplary external surface texture that takes the form of a series of raised elongate structures, which are roughly parallel to the longitudinal axis of the conductors 38, 40, 42. In various embodiments, other types of surface texture configurations can be utilized on the textured external surfaces of the outer insulative layers 52, 58, 60. For example, the insulative layers 52, 58, 60 can include surface texture typified by distinct, raised features on the outer surface of the insulative layer of a conductor. The surface texture can be uniform or non-uniform. Surface texture can, but need not, have a directionality associated with either or both the longitudinal axis of the material or the axis perpendicular thereto, and can include micron scale ridges, micronodules or raised features, for example, of any kind, rounded, flat-topped, or angular.

Adding surface texture or roughness to form the textured external surfaces 62, 64 and 66 results in these surfaces having different surface characteristics, in particular, different surface roughnesses, than the substantially smooth inner surface of the respective conductor lumen in which the particular conductor assembly is disposed. This differential surface roughness has been found to minimize frictional forces between these respective surfaces when they contact one another.

The presence of the texture on the textured external surfaces of the conductor assembly outer insulative layers, and the corresponding reduction in frictional resistance with respect to the adjacent inner surface of the conductor lumen, can also increase the manufacturability and ease of assembly of the lead assemblies. During the manufacture of lead assemblies, certain processing aids (e.g., vacuum, alcohol or other solvents, pressurized gases) are generally used in order to string one component co-radially through another, such as a cable conductor through a conductor lumen. The use of such processing aids may be time-consuming, costly and ineffective at reducing friction. Therefore, eliminating the need for such processing aids by reducing the friction between components during assembly of the medical devices or systems can be beneficial.

The specific configuration of the surface texture on the textured external surfaces 62, 64 and 66 can be based upon factors such as, without limitation, the types and sizes of the conductor members and the conductor lumens, the proximity of (e.g., clearance between) the textured external surfaces of the conductor assemblies to the inner surfaces of the conductor lumens, and other lead design and manufacturing considerations. In one exemplary embodiment that has been found to exhibit minimal frictional resistance between the conductor assemblies and the corresponding conductor lumen inner surfaces, the substantially smooth inner surface of the conductor lumen can have a roughness average (Ra) of less than 10 microinches, and the average surface texture roughness on the textured external surface of the outer insulative layer of the corresponding conductor assembly can be greater than about 16 microinches.

In various embodiments, the outer insulative layers can include or be formed from insulative materials such as, for example, ethylene tetrafluoroethylene (ETFE), polytetrafluoroethylene (PTFE), expanded PTFE (ePTFE), fluorinated ethylene propylene (FEP), perfluoro-alkoxy (PFA), polyvinylidene fluoride (PVDF), polyether ether ketone (PEEK), polyethylene terephthalate (PETE), silicone, and copolymers of the foregoing. In various embodiments, the outer insulative layers 52, 58, 60 can be extruded or molded onto the conductor members 38, 40, 42, or can be extruded or molded separately from the conductor members 38, 40, 42 which can then be strung within the extruded or molded insulative layers 52, 58, 60. The textured external surfaces 62, 64, 66 can be generated by extrusion dies that are machined to form the desired texture during the extrusion process. Alternatively, a mold can be texturized (e.g., by roughening the inner surface of the mold) and the resulting texture can then be transferred to the insulation layer during a molding process.

In another alternative embodiment, a smooth outer insulative layer may be extruded, coated or molded onto the conductor and subsequently altered, treated or roughened in order to provide texture to the layer. For example, an extruded or molded lead assembly component can undergo an embossing step after being produced. The embossing step can include applying the surface of the extruded lead component to a spiked roller in order to result in raised and lowered areas on the surface of the extruded or molded polymer. Another alternative step to introduce texture to an extruded or molded polymer surface can be to pass the extruded or molded polymeric component, before the component has solidified, through a die in order to include surface texture or roughness.

Another alternative subsequent method to extrusion or molding in order to introduce texture can be a grit-blasting process to create raised and lowered areas on a surface of an extruded or molded polymer. The grit material can be a sublimating material, such as frozen carbon dioxide particles, for example, in order to eliminate contamination of the surface of the extruded or molded polymer with embedded grit material. In short, the particular processes and equipment utilized to form the textured external surfaces of the outer insulative layers are not limited to a particular process or equipment.

Figure 4:
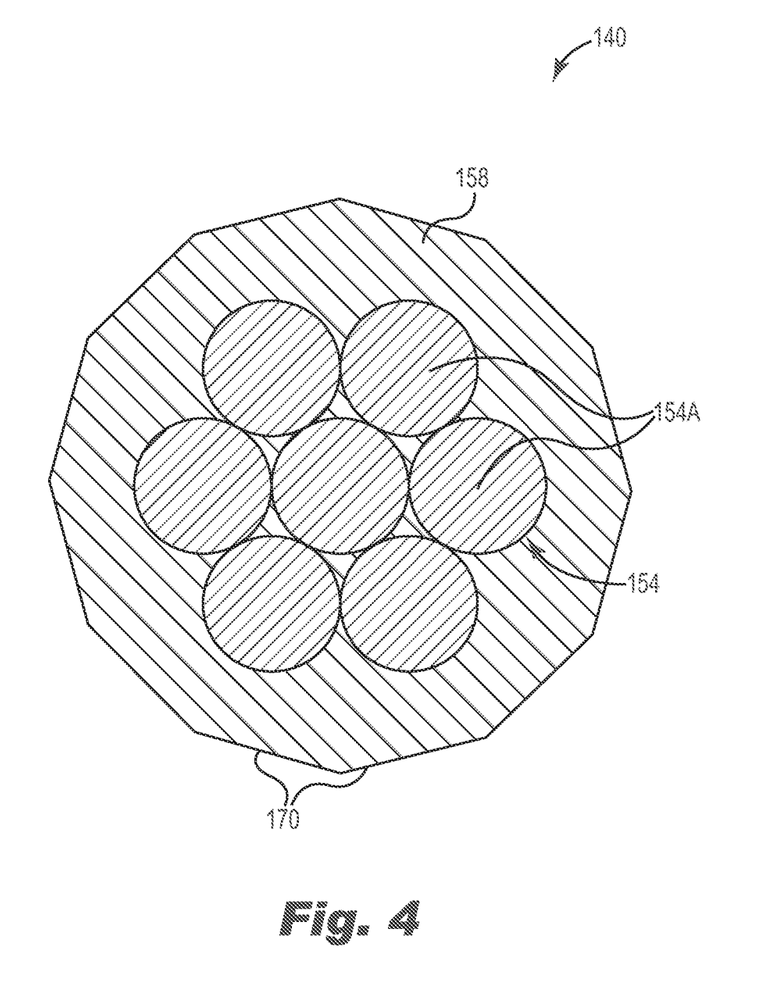
FIG. 4 is a cross-sectional view of a conductor including an insulative layer for use in the lead of FIG. 2, according to one embodiment.
Figure 5:
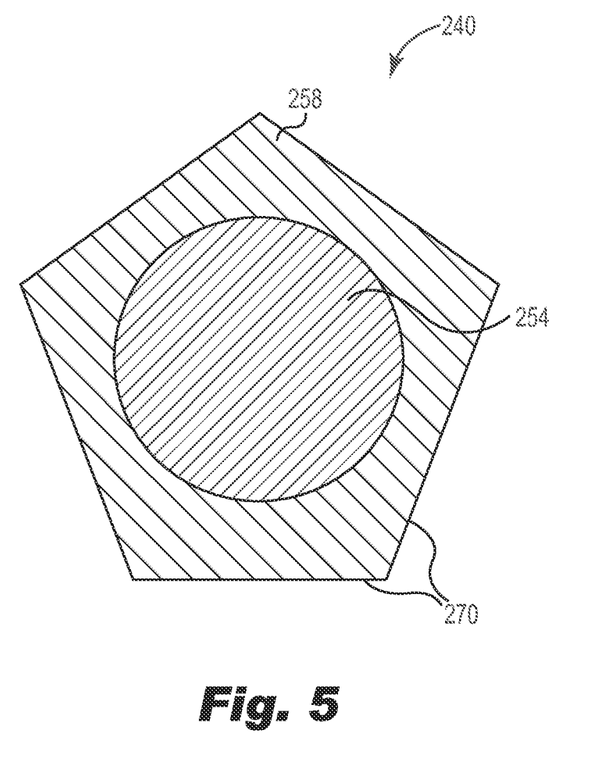
FIG. 5 is a cross-sectional view of a conductor including an insulative layer for use in the lead of FIG. 2, according to another embodiment.

FIGS. 4 and 5 illustrate alternative cross-sectional views of insulated cable conductor assemblies 140, 240, respectively, that may be included in the lead 14 in lieu of or in addition to either of the conductor assemblies 40, 42 discussed herein. As shown, the conductor assemblies 140, 240, respectively, have outer insulative layers 158, 258 with textured external surfaces configured to minimize the interfacial area between the inner surfaces of the respective conductor lumens and the outer insulative layers 158, 258.

As shown in FIG. 4, the conductor assembly 140 includes a multi-strand cable conductor member having a plurality of wires 154A wound together. As further shown, the outer insulative layer 158 axially surrounds the conductor wires 154A and includes a textured external surface defined by a plurality of surface segments 170 arranged about the longitudinal axis of the conductor assembly 140, with ridges between adjacent surface segments 170. The configuration of the outer insulative layer 158 is such that contact of the outer insulative layer 158 and the corresponding inner surface of the conductor lumen in which the conductor assembly 140 is disposed will be substantially confined to the ridges between adjacent surface segments 170, thus minimizing the contact area between these elements, which in turn operates to minimize frictional forces therebetween.

As shown in FIG. 5, the conductor assembly 240 includes a single wire conductor member 254, and the outer insulative layer 258 is disposed about the conductor member 254 and includes a textured external surface defined by a plurality of surface segments 270 arranged about the longitudinal axis of the conductor assembly 240, with ridges between adjacent surface segments 270. The configuration of the outer insulative layer 258, and in particular the presence of the ridges between the adjacent surface segments 270, operates in substantially the same manner as the outer insulative layer 158 to minimize friction between the outer insulative layer 258 and the inner surface of the lead body conductor lumen in which the conductor assembly 240 resides.

In the embodiments illustrated in FIGS. 4 and 5, the textured external surfaces of the outer insulative layers 158, 258 have, respectively, twelve (12) surface segments 170 and five (5) surface segments 270. The particular number of surface segments, however, can be varied within the scope of the various embodiments. Additionally, the cross-sectional shape of the outer insulative layers 158, 258 can be varied from the flat surface segment configuration with generally V-shaped ridges shown in FIGS. 4 and 5. For example, in various embodiments, the ridges between adjacent surface segments can be rounded or lobe-shaped. In various embodiments, the surface segments 170, 270 can have concave or convex cross-sectional profiles.

The outer insulative layers 158, 258 can be produced by extrusion about the respective conductor member 154, 254 using an extrusion die including an inner diameter with a design that results in the plurality of surface segments 170, 270. Alternatively, the outer insulative layers 158, 258 can be formed via molding operations utilizing a mold that includes texture to result in surface texture of the lead being the plurality of surface segments 170, 270.

Figure 6:
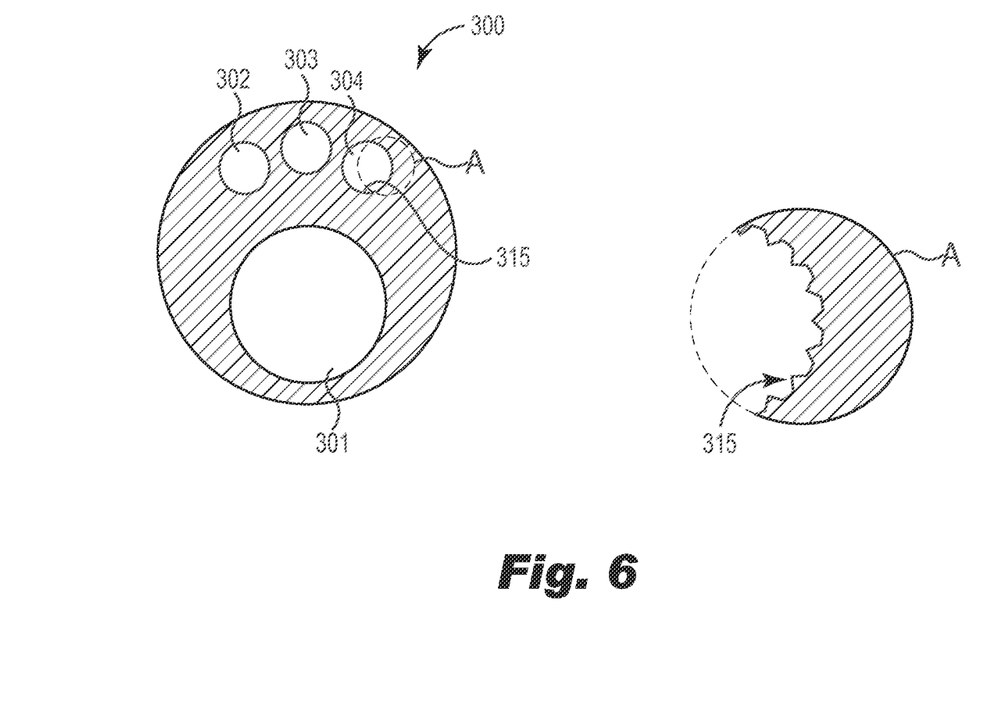
FIG. 6 is cross-sectional view of a lead body of the lead of FIG. 2, including an enlarged portion A illustrating surface features on an internal surface of a lead body lumen.

In the embodiments shown in FIGS. 2-5, the various conductor assemblies include outer insulative layers with textured external surfaces to reduce friction between the conductor assemblies and the lumens through which the conductor assemblies extend. Alternatively, or additionally, the inner surfaces of the respective conductor lumens can be textured or roughened in order to reduce friction with the conductors, which can have outer insulative layers that are substantially smooth (i.e., not textured). For example, FIG. 6 shows a lead body 300 with 4 lumens 301, 302, 303, 304. The enlarged area of detail A in FIG. 6 shows that the inner surface 315 of lumen 304 is textured. The other lumens 301, 302, 303 can be similarly textured. The texture can reduce friction between the corresponding conductor assembly and the inner surface of the conductor lumen 301, 302, 303, 304 in the same manner previously described with respect to embodiments in which the outer insulative layer of the conductor assembly has a textured external surface and the inner surface of the conductor lumen is substantially smooth.

In the various embodiments, the texture on the inner surface of the conductor lumen 301, 302, 303, 304 can be formed during extrusion or molding of the lead body 300. The die or mold (e.g., a core pin) used for extrusion or molding, respectively, can be configured with the desired texture in order to result in an inverse texture being located on an inner surface of an extruded lumen. Alternatively, texture or roughening of the inner surfaces of the respective conductor lumens 301, 302, 303, 304 can be applied after extrusion or molding of the lead body 300.

Figure 7:
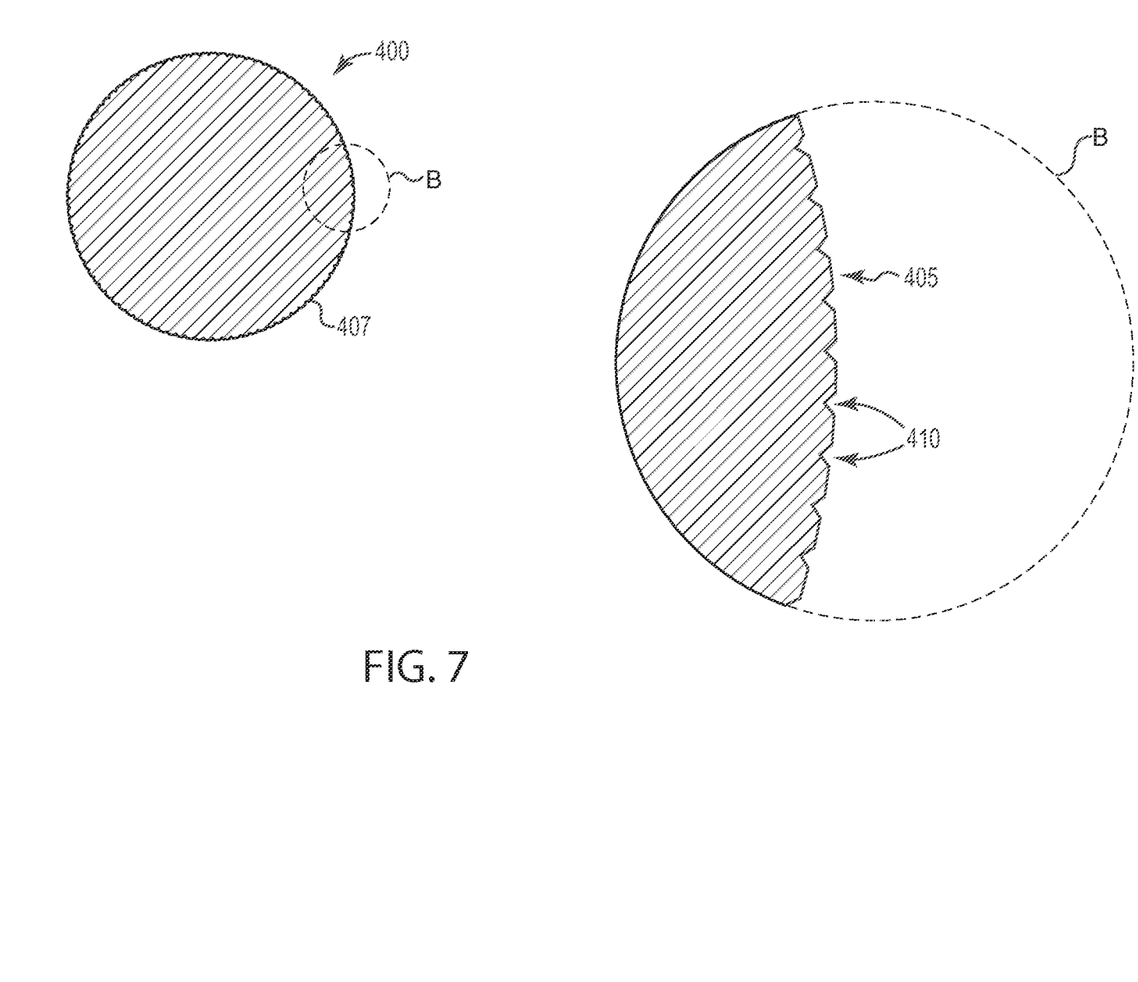
FIG. 7 is a cross-sectional view of a core or mandrel for use in forming a texture on the inside surface of a tubular medical device according to one embodiment.

While the embodiments illustrated in FIGS. 2-6 relate to implantable medical leads, the principles of the present disclosure can also be applied to other medical devices. For example, surface texture can be applied to an inner liner or inner surface of a lumen of a guide catheter in order to reduce surface friction between the inner surface of the guide catheter lumen and a lead or other medical device having a substantially smooth outer surface designed to be delivered or guided through the catheter. FIG. 7 shows an exemplary cross-section of a core 400 that can be used to produce a tubular liner 500 having a textured inner surface, an embodiment of which is shown in cross-section in FIG. 8, that can be used in a tubular medical instrument such as, for example, a catheter. In various embodiments, the core 400 can also be used to form the textured inner surfaces of the conductor lumens 301, 302, 303, 304 of the lead body 300.

In various embodiments, the core 400 can be made of Acetal (DELRIN™) for example, although other materials are possible. As shown, an exemplary texture 405 is present on an outer surface 407 of the core 400. As further shown in the enlarged area of detail B, the texture 405 can include indentations 410 sized and shaped as desired to provide a texture on the inner surface of the liner 500. The texture 405 can be applied to a full or a partial length and a full or partial radial circumference of the core 400.

In order to form the liner 500, a tubular piece of thermoplastic polymer, for example, can be placed over the textured core 400 and heated to re-flow into the texture 405 of the core 400. In various embodiments, the thermoplastic polymer may be a polyether block amide material, e.g., materials sold under the brand name PEBAX™, or a polyethylene material with a tie layer to PEBAX™, polyisobutylene based polyurethane (PIB-PU), or some other thermoplastic polymer. After the liner 500 is cooled and cured, the core 400 is pulled and removed from within the liner 500. The resulting liner 500 has a texture profile that is the inverse of the texture 405 on the core 400. In various other embodiments, the catheter liner 500 can be extruded or molded over the core 400.

Figure 8:
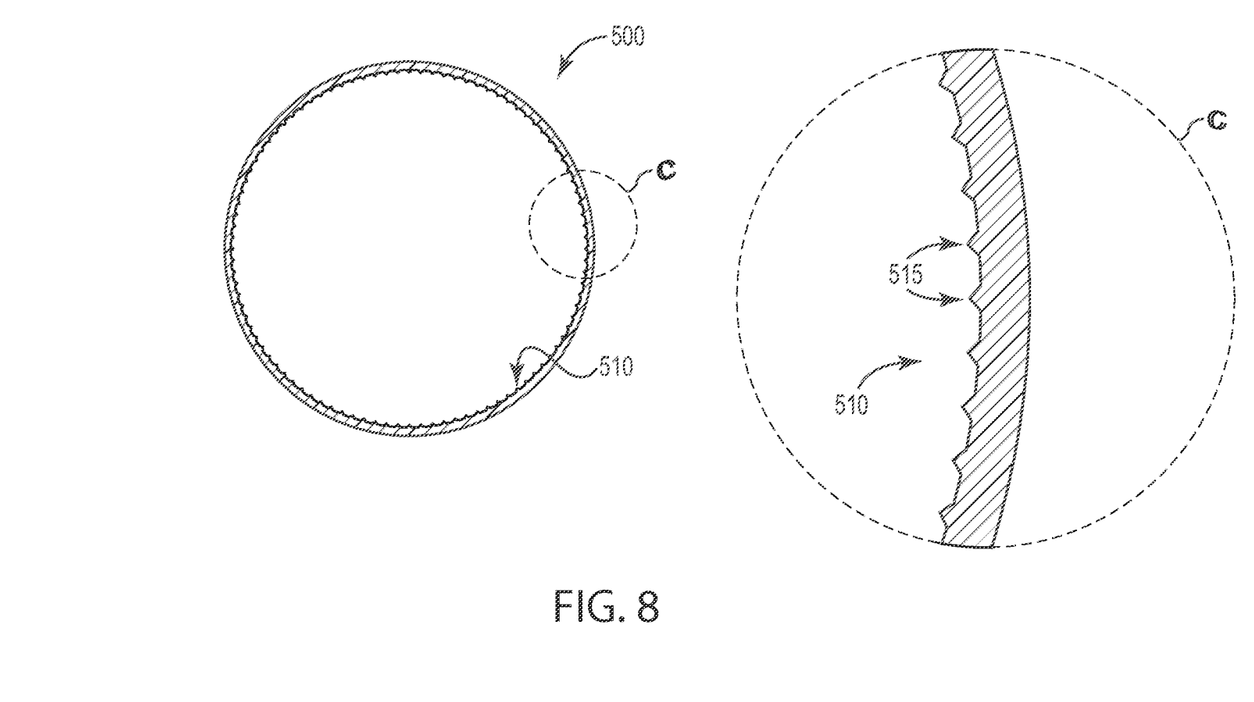
FIG. 8 is a cross-sectional view of a portion of an exemplary tubular medical device component showing a surface texture on an inside surface according to another embodiment.

As shown in FIG. 8, the liner 500 has an inner surface 510 with texture 515, which is shown in greater detail in enlarged area of detail C. Once formed, the liner 500 can be placed or strung within a tubular polymeric jacket to form a guide catheter shaft. Alternatively, the liner 500 may be covered by one or more segments of a polymeric material to form the completed guide catheter shaft. Still other techniques for forming a completed guide catheter shaft including the liner 500 can be used within the scope of the present disclosure.

The texture 515 on the liner 500 can reduce surface friction between the inner surface of the liner 500 and another device (e.g., a lead, catheter, guide wire, balloon angioplasty device, etc.) slidably disposed therein. The reduction in the coefficient of friction results in less force being used to move the other device through the catheter, which can result in more precise use of the device by a user.

The configuration of the texture 515 can be varied and optimized for the particular clinical use of the corresponding catheter. Various exemplary cross-sections of single extruded or molded texture profiles are shown schematically in FIGS. 9A-H. As shown, the various surface textures are defined by a plurality of protrusions disposed about and extending radially inward with respect to the longitudinal axis of the liner 500. In the various embodiments, the protrusions are shaped to minimize contact area and frictional resistance between the textured inner surface of the corresponding catheter lumen and a medical device (e.g., a guide wire, catheter, stimulation lead, and the like) disposed within the catheter lumen.

Figure 9A:
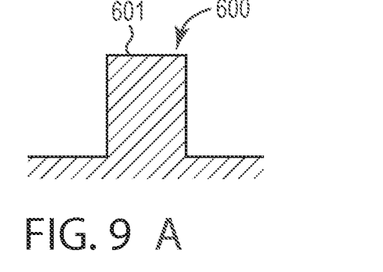
FIGS. 9A-9H are cross-sectional elevation views of exemplary texture protrusion profiles according to various embodiments.
Figure 9B:
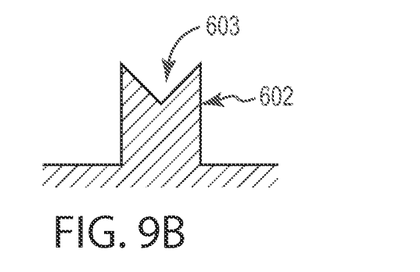
Figure 9C:
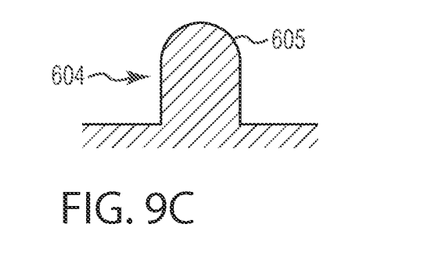
Figure 9D:
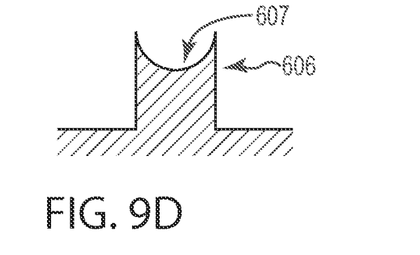
Figure 9E:
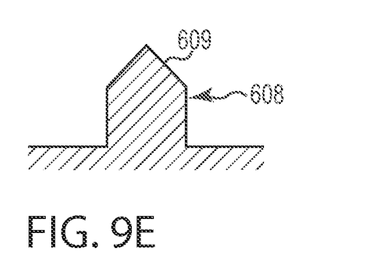
Figure 9F:
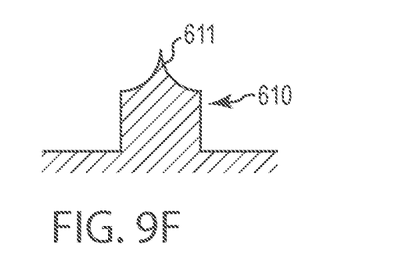
Figure 9G:
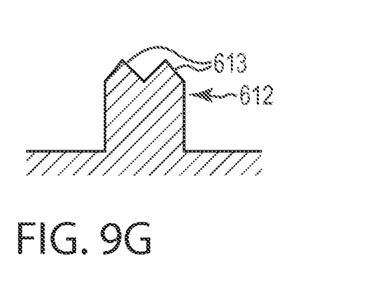
Figure 9H:
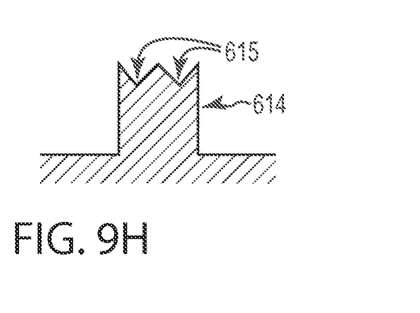

FIG. 9A shows a cross-section of a protrusion 600 having a generally flat, upper surface 601. FIG. 9B shows a protrusion 602 having a single triangular-shaped depression 603 along its length. FIG. 9C shows a protrusion 604 with a rounded, convex-shaped upper surface 605. FIG. 9D shows a protrusion 606 having a concave depression 607 along its length. FIG. 9E shows a protrusion 608 having a triangular-shaped extension 609. FIG. 9F shows a protrusion 610 that includes two concave curves along the length that result in the protrusion extending outward generally as a linear extension 611 along its longitudinal length. FIG. 9G shows a protrusion 612 having two triangular-shaped extensions 613. FIG. 9H shows a protrusion 614 with two triangular-shaped depressions 615. Other suitable shapes of protrusions can be used, and are not limited to those shown.

In the various exemplary embodiments shown in FIGS. 9A-9H, the various protrusion profiles form, in effect, channels or reservoirs for receiving a fluid, e.g., saline, that may be introduced into the respective catheter lumen as part of the medical procedure in which the catheter is used. Relative motion of the catheter and the elongate medical device (e.g., a guide wire, lead or other catheter) disposed within the lumen thereof can tend to cause the fluid to be drawn over and across the protrusions by hydrodynamic forces. This moving saline creates a lubricating force that can tend to push the elongate medical device away from the textured inner surface of the catheter, thus further minimizing friction between the respective surfaces.

In various embodiments, the particular texture can be molded or extruded such that the texture extends generally longitudinally along the component. Alternatively, the extruded or molded texture can extend helically along or around the surface of the elongated component, e.g., by rotating the core 400 or the extruded polymer component during the extrusion process.

Figure 10:
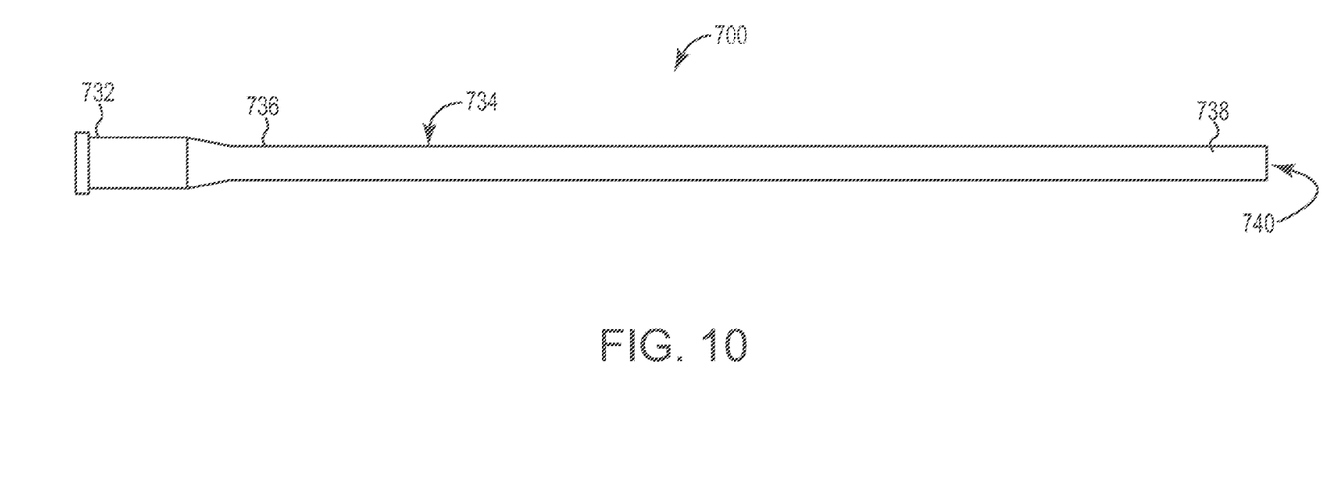
FIG. 10 is a side view of a guide catheter that can include a textured inner surface according to one embodiment.

FIG. 10 illustrates an exemplary guide catheter that can have texture on an inner luminal surface. Guide catheter 700 is tubular and has a hub 732, a shaft 734, a proximal end 736 and a distal end 738. Texture (not visible in FIG. 11) can be present on an inner surface of an inner lumen 740 of the shaft 734. In one embodiment, the catheter shaft 734 includes the liner 500 such that the inner surface of the inner lumen 740 has an inner surface texture to minimize friction between the inner surface and another device disposed and movable within the catheter shaft 734. In one embodiment, the catheter shaft 734 is a unitary structure including the textured inner surface described herein but without requiring the inclusion of the separate liner 500. In various embodiments, the textured inner surface can extend along all or only one or more portions of the length of the catheter shaft 734.

While the embodiments of FIGS. 7-10 relate to medical devices having textured internal surfaces, a surface texture configured to lower the coefficient of friction between components can also be located on an outer surface of one or more components of a medical device system that may contact each other. For example, two or more components or devices (e.g., balloon catheters, leads, ablation devices, stents) may extend through a single guide or delivery catheter. One or more than one of the components can include texture on an outer surface to reduce friction between the components themselves and between the components and an inner luminal surface of the guide or delivery catheter.

Figure 11:
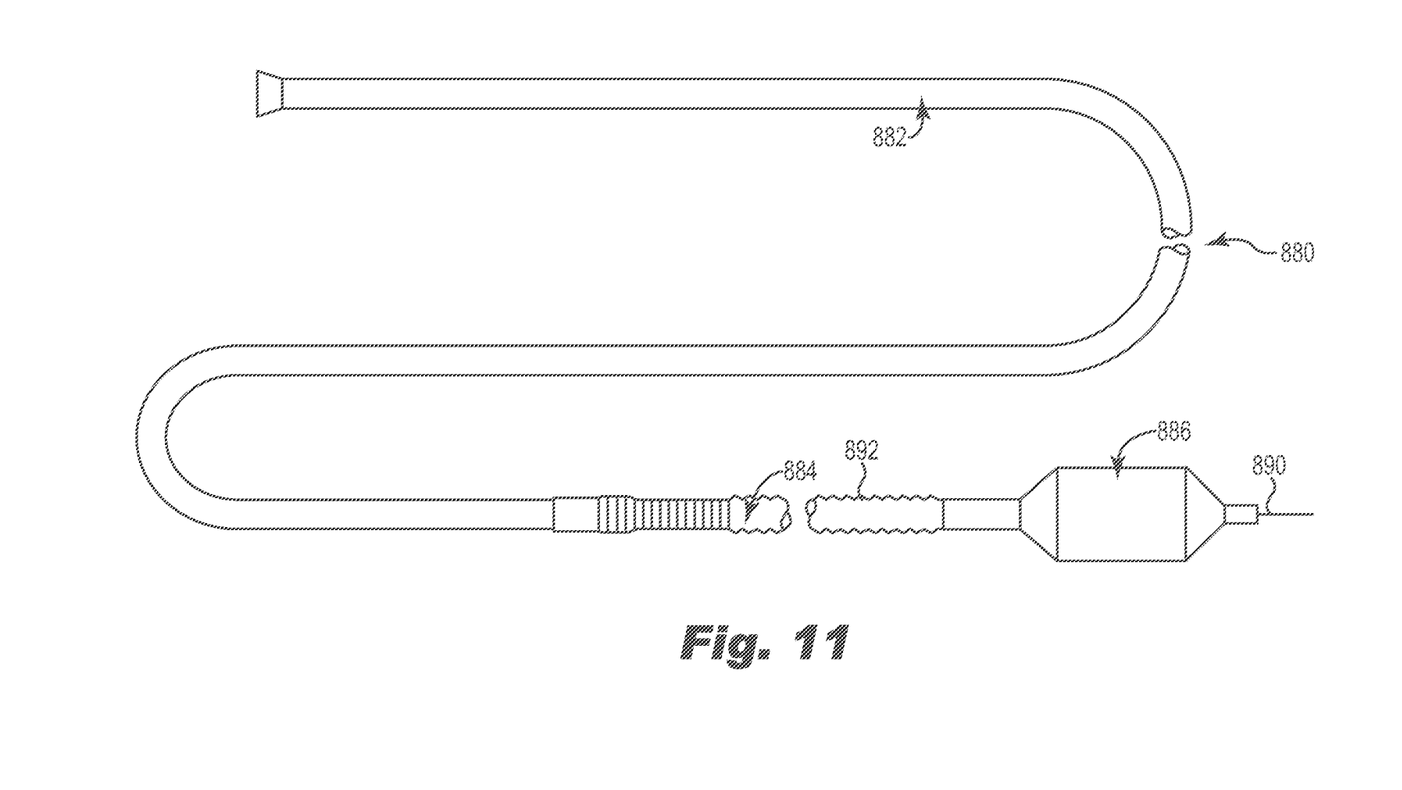
FIG. 11 is a side view of an exemplary balloon dilation catheter having a textured external surface according to one embodiment.

An example of a system including components that may include such texture on an outer surface of one or more components is a dual balloon catheter system, which may be deployed through a common guide catheter. In such embodiments, one or both of the balloon catheters may include texture on at least a portion of their outer surface. FIG. 11 illustrates an exemplary balloon dilatation catheter 880. The catheter 880 has a main shaft section 882, an intermediate sleeve section 884 and a distal balloon section 886. The catheter 880 is adapted for over-the-wire applications, and as such is configured to be deployed using a guidewire 890 slidably disposed within an inner lumen (not shown) of the catheter 880. The catheter 880 can include a friction-reducing texture 892, for example, as shown, on its intermediate sleeve section 884, which section, in use, slidably contacts a surface of another device and/or a guide catheter through which the balloon dilatation catheter 880 is deployed. In various embodiments, additional regions of the outer surface of the balloon dilatation catheter 880 can include a friction-reducing surface texture. In various embodiments, the inner lumen (not shown) of the catheter 880 can include a textured inner surface according to the various embodiments described herein, which can result in minimizing frictional forces between the textured inner surface of the catheter 880 and the guidewire 890 as the catheter 880 is deployed by an over-the-wire technique.

Figure 12:
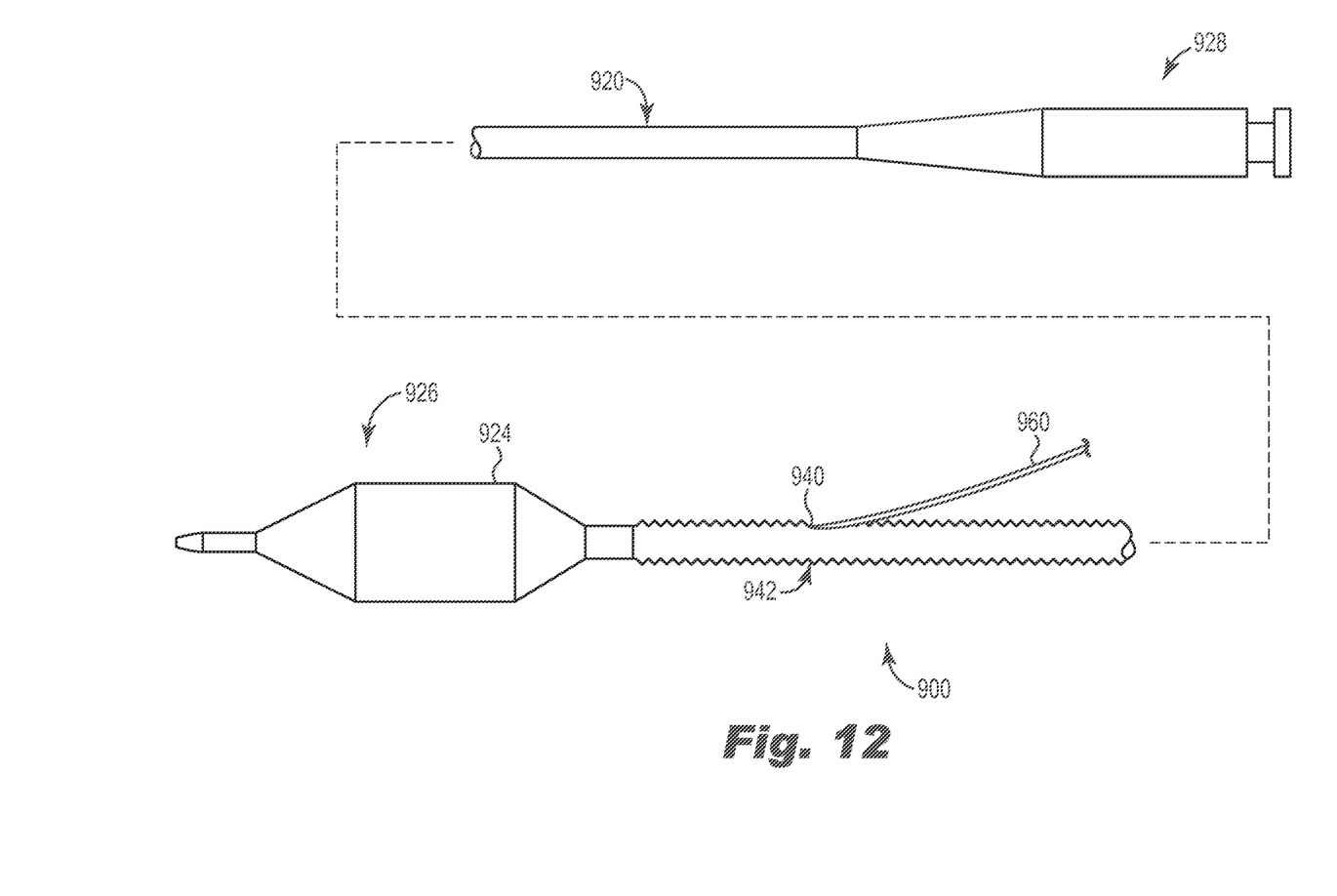
FIG. 12 is a side view of an exemplary monorail balloon dilatation catheter having a textured external surface according to one embodiment.

FIG. 12 illustrates a monorail balloon catheter 900 including an elongated catheter shaft 920 having proximal 928 and distal 926 ends, and a balloon 924. The balloon 924 is at the distal end portion 926 of the catheter 900. A guide wire 960 is shown introduced into guide wire port 940, and can extend out the distal end of the catheter 900. In various embodiments, the monorail balloon catheter 900 can be deployed alone, or in combination with another balloon catheter (e.g., the balloon dilatation catheter 880 discussed herein) within a common guide catheter. Accordingly, in various embodiments, a texture 942 can be present on the shaft 920 at or near the distal end portion 926 to minimize friction between the balloon catheter 900 and other adjacent surfaces in which the shaft 920 may come into sliding contact during deployment, according to the various embodiments described herein. In various embodiments, the surface texture 942 operates to reduce friction between the textured outer surface of the shaft 920 and the outer surface of the guide wire 960 proximate the guide wire port 940.

It will be readily appreciated, based on the present disclosure, that additional components and medical devices can advantageously be formed with textured inner or outer surfaces to minimize friction between such surfaces and adjacent surfaces during use. Thus, the various embodiments thereof are not limited to those specifically shown and described herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. An implantable medical lead comprising:
   a lead body having a conductor lumen having a substantially smooth inner surface;
   a conductor assembly extending through the conductor lumen, the conductor assembly including a conductor member and an outer insulative layer disposed about the conductor member, the outer insulative layer including a textured external surface; and
   an electrode on the lead body coupled to the conductor member,
   wherein the textured external surface has a surface roughness average greater than 16 microinches and the inner surface of the conductor lumen has a surface roughness average less than 10 microinches.

2. The implantable medical lead of claim 1, wherein the textured external surface includes a plurality of raised surface features.

3. The implantable medical lead of claim 2, wherein the plurality of raised surface features extend longitudinally along the conductor assembly.

4. The implantable medical lead of claim 2, wherein the raised surface features extend in a helical pattern longitudinally along the conductor assembly.

5. The implantable medical lead of claim 1, wherein the outer insulative layer comprises a polymeric element extruded about the conductor member.

6. The implantable medical lead of claim 1, wherein the outer insulative layer comprises a polymeric element molded about the conductor member.

7. The implantable medical lead of claim 1, wherein the outer insulative layer has a cross-sectional shape defined by a plurality of generally flat surface segments arranged about a longitudinal axis of the conductor assembly, with a ridge disposed between adjacent generally flat surface segments.

8. The implantable medical lead of claim 1, wherein the conductor member comprises a multi-strand cable or wire coil about which the outer insulative layer is extruded.

9. A method of forming an implantable medical lead, the method comprising:
   forming a conductor assembly by extruding a tubular polymeric outer insulative layer over a conductor member through an extrusion die configured to form a textured external surface on the outer insulation layer;
   disposing the conductor assembly within a conductor lumen of an insulative lead body, wherein the conductor lumen has a substantially smooth inner surface; and
   coupling an electrode to the conductor member and the lead body,
   wherein the textured external surface of the outer insulative layer is configured to minimize frictional forces between the textured external surface and the inner surface of the conductor lumen, wherein the textured external surface has a surface roughness average greater than 16 microinches and the inner surface of the conductor lumen has a surface roughness average less than 10 microinches.

10. The method of claim 9, wherein forming the conductor assembly includes extruding the tubular polymeric outer insulative layer having a cross-sectional shape defined by a plurality of generally flat surface segments arranged about a longitudinal axis of the conductor assembly, with a ridge disposed between adjacent generally flat surface segments.

11. The method of claim 9, wherein the textured external surface is characterized in part by a plurality raised surface features that extend longitudinally along the conductor assembly.

12. The method of claim 9, wherein the textured external surface is characterized in part by a plurality of raised surface features that extend in a helical pattern longitudinally along the conductor assembly.

13. A method of forming an implantable medical lead, the method comprising the steps of:
   disposing a tubular-shaped polymeric outer insulative layer onto a conductor member;
   adding a surface texture to at least a portion of an outer surface of the outer insulative layer;
   disposing the conductor member with the outer insulative layer disposed thereon within a conductor lumen of an insulative lead body, wherein the conductor lumen has a substantially smooth inner surface; and
   coupling an electrode to the conductor member and the lead body,
   wherein the surface texture is configured to minimize friction between the outer insulative layer and the inner surface of the conductor lumen, wherein the textured external surface has a surface roughness average greater than 16 microinches and the inner surface of the conductor lumen has a surface roughness average less than 10 microinches.

14. The method of claim 13, wherein the step of adding the surface texture to the outer surface of the outer insulative layer comprises passing the conductor member and insulative layer together through a die that is configured to add the surface texture to the outer surface of the outer insulative layer.

15. The method of claim 13, wherein the texture includes a plurality of raised surface features.

16. The method of claim 13, wherein the step of adding the surface texture to at least a portion of the outer surface of the outer insulative layer includes forming the outer insulative layer having a cross-sectional shape defined by a plurality of generally flat surface segments arranged about a longitudinal axis of the conductor assembly, with a ridge disposed between adjacent generally flat surface segments.

17. The method of claim 13, wherein the step of disposing the outer insulative layer onto the conductor member includes extruding the outer insulative layer onto the conductor member.

18. The method of claim 13, wherein the step of disposing the outer insulative layer onto the conductor member includes molding the outer insulative layer onto the conductor member.

19. The method of claim 13, wherein the conductor member comprises a multi-strand cable.

* * * * *